United States Patent [19]

von Gutfeld et al.

[11] Patent Number: 4,512,197
[45] Date of Patent: Apr. 23, 1985

[54] APPARATUS FOR GENERATING A FOCUSABLE AND SCANNABLE ULTRASONIC BEAM FOR NON-DESTRUCTIVE EXAMINATION

[75] Inventors: Robert J. von Gutfeld, New York; Sherman S. Wang, Pleasantville, both of N.Y.

[73] Assignee: The United States of America as represented by the Secretary of the Navy, Washington, D.C.

[21] Appl. No.: 528,708

[22] Filed: Sep. 1, 1983

[51] Int. Cl.³ .................. G01N 29/00; G10K 10/00
[52] U.S. Cl. ........................................ 73/643; 73/601
[58] Field of Search .................................. 73/643, 601

[56] References Cited

U.S. PATENT DOCUMENTS

| | | | |
|---|---|---|---|
| 3,978,713 | 9/1976 | Penney | 73/643 |
| 4,121,469 | 10/1978 | Kaule et al. | 73/643 |
| 4,137,991 | 2/1979 | Melcher et al. | 73/643 |
| 4,169,662 | 10/1979 | Kaule et al. | 73/643 |
| 4,255,971 | 3/1981 | Rosencwaig | 73/643 |
| 4,269,067 | 5/1981 | Tyman et al. | 73/643 |
| 4,448,525 | 5/1984 | Mikosuba et al. | 73/643 |

*Primary Examiner*—Howard A. Birmiel
*Attorney, Agent, or Firm*—Robert F. Beers; Henry Hansen; Vincent T. Pace

[57] ABSTRACT

An apparatus for generating a focusable and scannable ultrasonic beam for use in nondestructive internal examination of an object. In one embodiment an optical mask modifies a pulsed light beam to form an optical zone pattern. The zone pattern is imaged on the surface of an optically absorbing thermoelastic layer in contact with a propagation medium. An ultrasonic beam is thereby generated which focuses at a point in an object submerged in the propagation medium. An optical lens and a mirror respectively focus and scan the modified light beam, whereby the ultrasonic beam is also focused and scanned. A second embodiment utilizes an acousto-optic modulator to modify the light beam and cause scanning and focusing of the ultrasonic beam. Suitable detectors and instrumentation may be provided to analyze the ultrasonic beam after it has traversed the object under examination.

13 Claims, 6 Drawing Figures

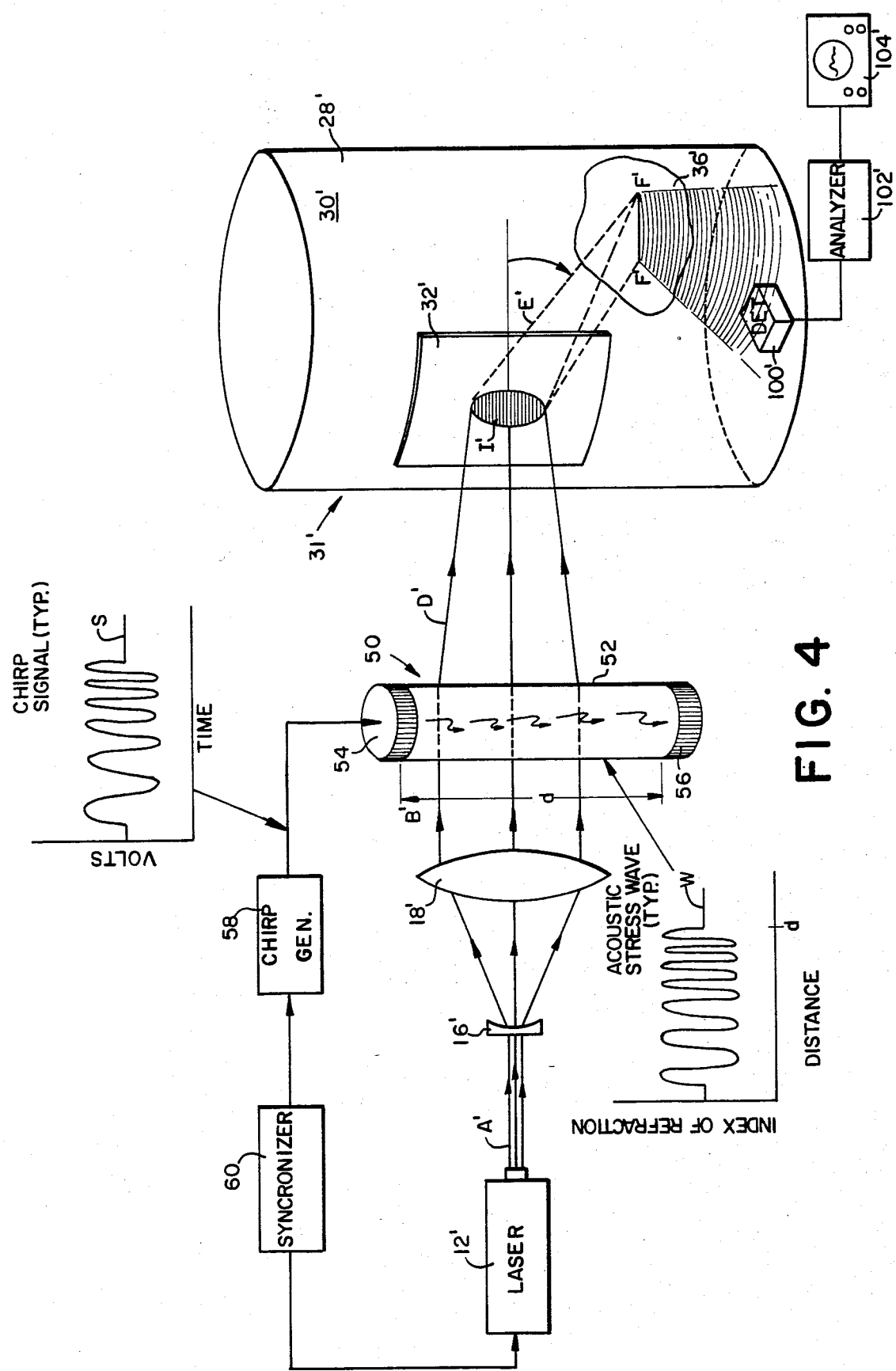

APPARATUS FOR GENERATING A FOCUSABLE AND SCANNABLE ULTRASONIC BEAM FOR NON-DESTRUCTIVE EXAMINATION

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates generally to ultrasonic examination of opaque materials, and more particularly to small ultrasonic beams which are both focusable and scannable so as to be suitable for detecting small defects.

An important application of ultrasonics is examining opaque materials and tissue for internal flaws and abnormalities. The examination of materials for flaw detection as well as the examination of tissue for medical diagnostic purposes are improved by the use of small acoustic beams which can be scanned and focused. Such small acoustic beams are desirable in order to detect small defects.

Most of the current methods of ultrasonic examination make use of the well-known Bragg-diffraction effect. In these devices and systems an unfocused, non-scanning ultrasonic beam is propagated in a medium which contains an article or sample to be examined. A light beam is then directed through the medium which is usually transparent. As the light beam traverses the medium, it is diffracted by the ultrasonic waves which have been reflected or scattered by the sample. The resulting diffracted light beam can then be processed and analyzed to render a visual image of the interior of the article examined.

A major drawback to these methods is that the ultrasonic beam is not focusable or scannable, thus small defects are difficult, if not impossible to detect.

Other types of systems using only ultrasonic beams require either mechanical movement of a single element transducer or use of an array transducer to provide scanning of the ultrasonic beam. The single element transducer, however, is usually slow and cumbersome, and does not readily provide for varying the focus of the ultrasonic beam. The array transducer, while it provides some focusing of the ultrasonic beam, can be cumbersome and very expensive.

More recently, small acoustic beams obtainable by laser-generated thermoelastic expansion have been found useful in nondestructive examination of materials. A system utilizing this principle is described in U.S. Pat. No. 4,137,991 to Melcher et al. However, no practical means for scanning and focusing the thermoelastic waves is available except by use of expensive arrays.

SUMMARY OF THE INVENTION

Accordingly, one object of this invention is to generate small ultrasonic beams for examining the interior of opaque materials.

Another object of this invention is to focus and scan the generated ultrasonic beam.

A further object of this invention is to generate small ultrasonic beams by laser-produced thermoelastic expansion of a thin film layer in contact with water.

A still further object of this invention is to detect small flaws and abnormalities in opaque materials.

The above and other objects are realized in the present invention by a laser-generated light beam which is modified to form an optical zone pattern. The optical zone pattern may be formed by such methods as transmitting the light beam through a mask having alternating reflecting and transmitting regions, or transmitting the light beam through an acousto-optic modulator.

The modified light beam is then directed onto the surface of an optically-absorbing thermoelastic layer in contact with water. An image of the optical zone pattern is formed on the surface. A series of acoustic waves is thereby generated in the water which converge and focus at a particular point in an article immersed in the water.

The light and dark region spacing of the optical zone pattern is designed to produce acoustic waves of a predetermined wavelength. The depth of focus is varied by changing the size of the image of the zone pattern, while maintaining the same ratio between light and dark zone radii. The ultrasonic beam is scanned either by mechanical means, such as an oscillating mirror, or by changing the zone pattern image by means of an acousto-optic modulator.

Other objects, advantages, and novel features of the invention will become apparent from the detailed description of the invention which follows the accompanying drawings wherein:

BRIEF DESCRIPTION OF THE DRAWINGS

FIG. 4 shows another embodiment according to the invention; and

DETAILED DESCRIPTION OF THE INVENTION

Figure 1:
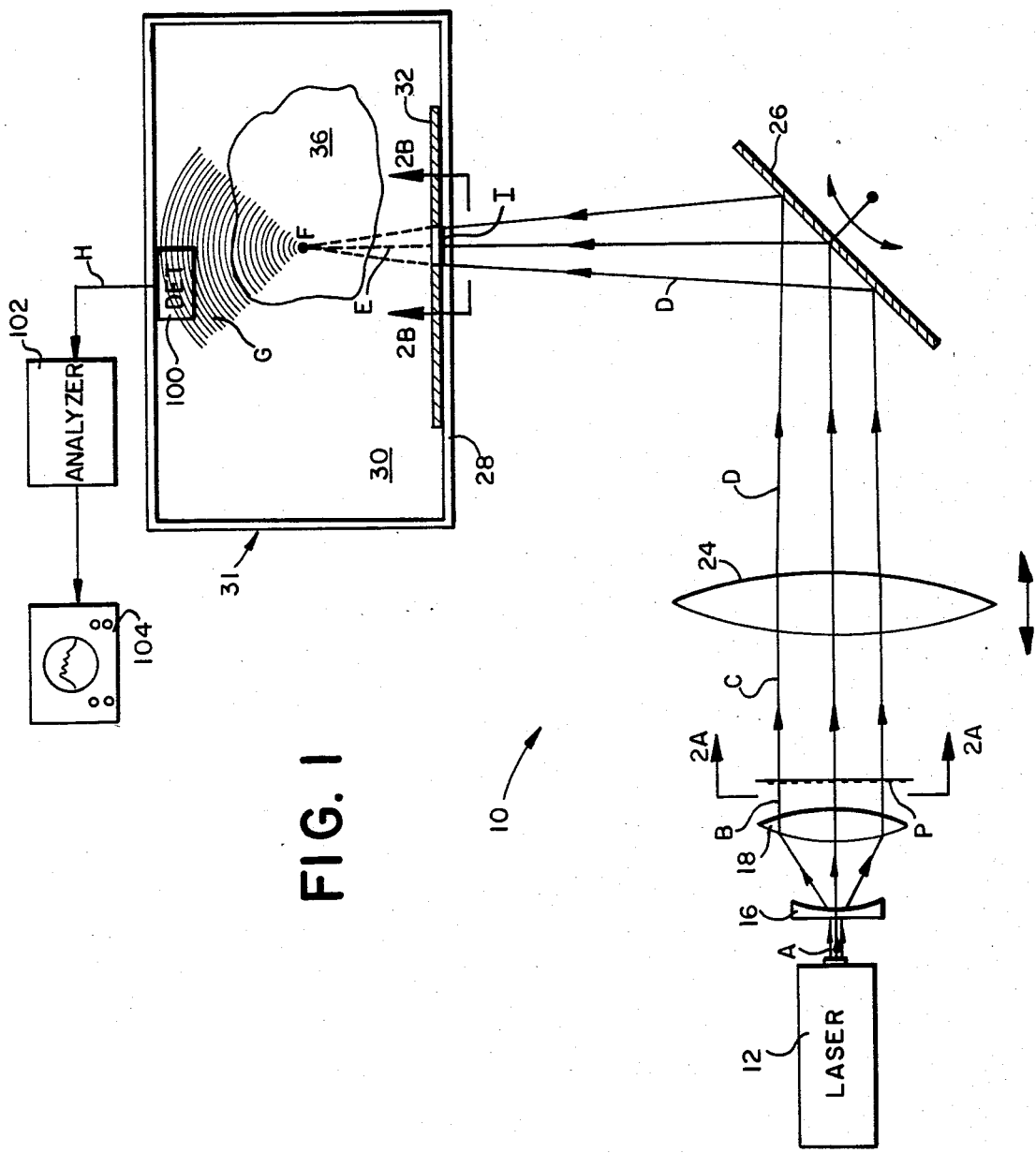
FIG. 1 shows one embodiment according to the invention for ultrasonic examination.

Referring now to the drawings, and in particular to FIG. 1, there is shown generally an ultrasonic beam generating device 10 according to the present invention. The device 10 has a pulsed laser 12 which generates a coherent light beam A which passes through a diverging lens 16 and a collimating lens 18 to produce an expanded and collimated beam B.

Beam B is then directed through a mask 20 having a zone pattern P. The pattern P may be formed by exposing photographic film or by evaporation deposition on a transparent substrate.

Figure 2A:
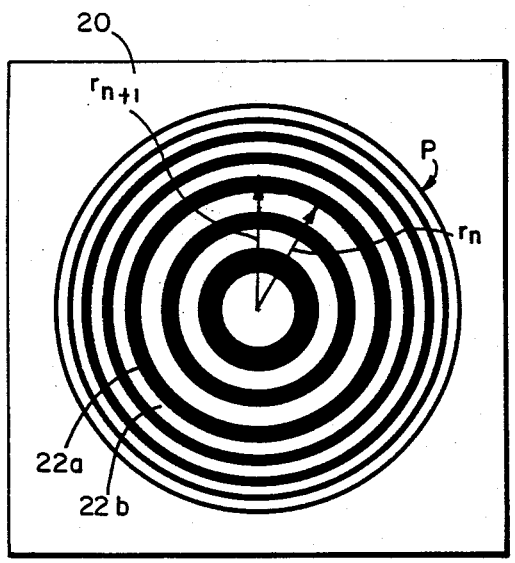
FIG. 2A is a plane view of an optical mask in the embodiment of FIG. 1.

The pattern P produced on mask 20 is shown more clearly in FIG. 2A. Pattern P has light reflecting (or absorbing) ring zones 22a alternating with light transmitting ring zones 22b. The pattern P is designed such that the radii of the light and dark rings bear the relationship $$r_n/r_{n+1} = \sqrt{\frac{n}{n+1}},$$

where $r_n$ is the inner radius of the $n^{th}$ ring zone, and $r_{n+1}$ is the inner radius of the next larger ring zone.

As the light beam B passes through the mask 20 it is modified and will appear identical to the pattern P when imaged on the surface.

The modified light beam C is directed through a focusing lens 24 which is slidably disposed between mask 20 and an oscillating mirror 26. The size of beam C projected onto mirror 26 is ajdusted by moving lens 24 along demagnified beam D toward or from mask 20.

Beam D is refleced by mirror 26 toward a thermoelastic thin film layer 32 applied to a transparent wall 28 of a vessel 31. Vessel 31 contains an acoustic propagation medium 30 such as water in contact with layer 32 and in which an object 36 to be examined is fully submerged.

Thin film layer 32 generally consists of a material which is optically absorbing and has a high coefficient of thermal expansion. Such materials as graphite, black epoxy paint or a rubber membrane would be suitable.

Figure 2B:
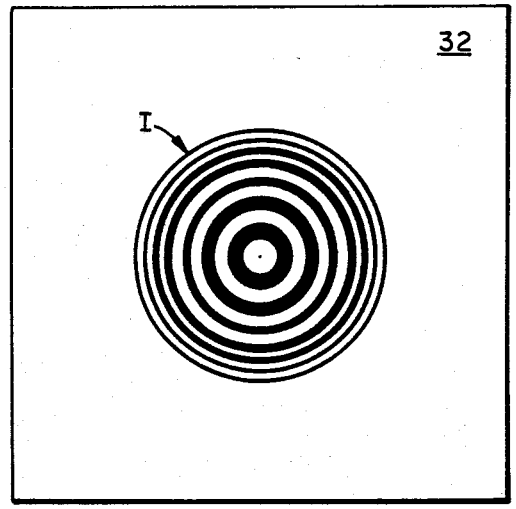
FIG. 2B is a plane view of an image projected by a modified light beam on a thermoelastic surface in the embodiment of FIG. 1.

As beam D impinges on the surface of layer 32, an image I of the optical zone pattern induced by mask 20 is formed. Image I would appear as shown in FIG. 2B, a demagnified image of the zone pattern P. Thermoelastic ultrasonic waves are thereby generated in medium 30 to form an ultrasonic beam E which is focused at a point F on the object 36 to be examined.

Generation of the ultrasonic waves is based on the fact that when a pulse of energy is rapidly delivered onto the surface of certain materials in contact with an acoustic medium there is a rapid thermal expansion of the surface. This rapid expansion produces a nonequilibrium stress distribution which results in a stress wave being propagated through the material and transmitted through the acoustic medium. By generating laser pulses of sufficiently long duration, for example greater than 0.1 $\mu$sec, and sufficiently high power density, approximately $10^6$ peak watts/cm$^2$, it is possible to generate detectable ultrasonic pulses in the megahertz frequency range without any substantial material damage.

Figure 3:
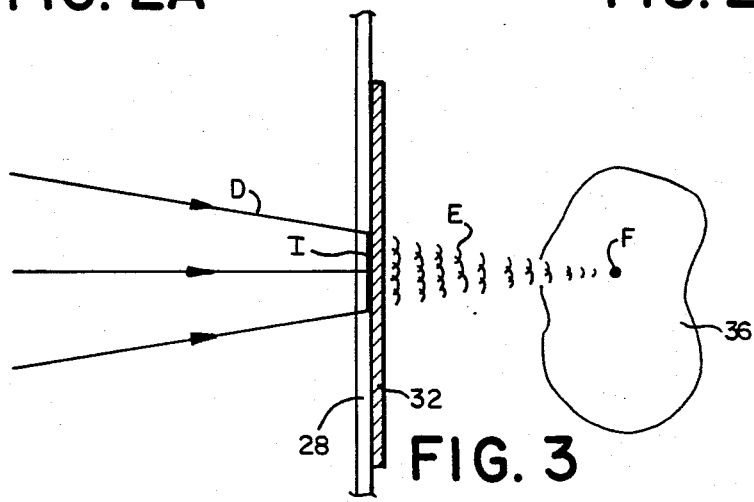
FIG. 3 illustrates the propagation of an ultrasonic beam by a light beam impinging on a thermoelastic layer in the embodiment of FIG. 1.

The phenomenon is illustrated in FIG. 3 wherein the modified laser beam D travels through the transparent vessel wall 28 and impinges on the absorbing thin film 32. The image I of the optical zone pattern is formed on the surface of film 32. By virtue of the thermoelastic effect, a series of ultrasonic waves forming a beam E is propagated. Beam E converges at a focal point F on the object 36 to be examined due to constructive interference.

The zone pattern P is designed also to produce an acoustic signal having a wavelength $\lambda$ in the propagation medium 30. Thus, as in FIGS. 1 and 2B, the optical zone pattern image I will give rise to an acoustic zone or ring pattern which will provide a focusing of the ultrasonic waves at a focal length $b \approx r_1^2/\lambda$. The radii of successive zones can be determined from $r_n = \sqrt{n\ b\lambda}$. Thus, once the wavelength $\lambda$ and the focal length b are selected the interference pattern can be designed.

The oscillating mirror 26 in FIG. 1 is used to scan the beam D over the small regions in the plane of the absorbing thin film layer 32. As discussed above, the focusing lens 24 is moved along the axis of beam D to alter the size of the optical zone pattern image I. The zone radii in image I will remain in the same ratio, but there will be a new thermoelastic focal depth. In this manner three dimensional scanning of the object 36 is achieved.

The ultrasonic beam E generated by the subject invention impinges on the object 36, passes through it, and emerges an ultrasonic beam G. An acoustic detector 100, located inside vessel 31, receives the ultrasonic signal of beam G and converts it to an electrical signal H. The acoustic detector 100 may be realized by such devices as a hydrophone or a piezoelectric transducer. The electrical signal H is then processed by suitable instrumentation such as a spectrum analyzer 102 and displayed on an oscilloscope 104.

FIG. 4 illustrates another, slightly more complex embodiment of the subject invention. A laser 12' generates a pulsed light beam A' which is expanded by diverging lens 16' and collimated by collimating lens 18'. The expanded and collimated beam B' is then directed through an acousto-optic modulator 50.

The acousto-optic modulator 50 comprises a water column 52 of height d. At one end of the water column 52 there is mounted an acoustic absorber 56. At the other end there is a piezoelectric transducer 54. Alternatively, the acousto-optic modulator 50 may simply consist of a transparent piezoelectric crystal of height d.

An acoustic chirp signal generator 58 is connected to the transducer 54. The light beam B' is modulated by a chirp signal S. This acousto-optic modulation occurs in certain materials in which the index of refraction varies significantly with an applied stress. Water is one such material. Then when the chirp signal S is transmitted to the piezoelectric transducer 54 the index of refraction of the water is varied along the height d. As the light beam B' passes through the water column 52 its crossectional intensity is modified to form an optical zone pattern.

A vessel 31' is provided containing an acoustic propagation medium 30' such as water and an object 36' to be examined totally submerged therein. The vessel 31' has a transparent wall 28' to which is applied a thin absorbing film 32'. The thin film 32' is located such that it will be in the path of the light beam d' after it has passed through the acousto-optic modulator 50.

As the beam D' strikes the surface of the thin film 32' it forms an optical zone pattern image I'. As in the first embodiment, once the image I' is formed on the thin film 32', a thermoelastic wave E' is produced which propagates through the adjacent medium 30' and converges to a focal line (e.g. line F'—F') on the object 36' to be examined.

Alternatively, if a point focus is desired a transducer array could be used in the acousto-optic modulator 50 instead of the single transducer 54. If each transducer in such an array is separately chirped, then the zones of the optical zone pattern image I' will be curved. The ultrasonic waves propagated would then converge to a point instead of a line.

Figure 5:
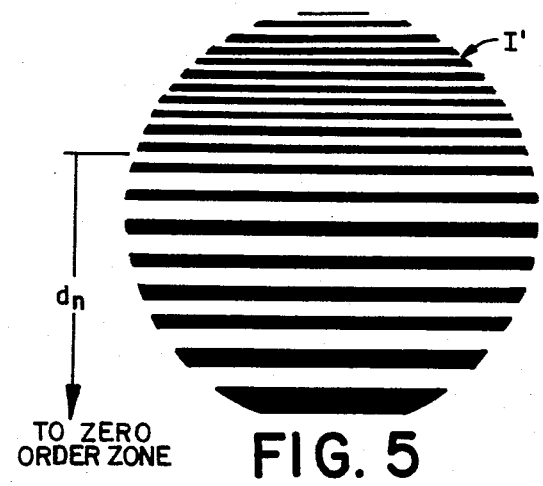
FIG. 5 shows a typical image of the optical zone pattern generated in the embodiment of FIG. 4.

The ultrasonic beam E' is focused by changing the zone spacing of the image I'. This is accomplished by changing the modulating chirp signal S. FIG. 5 illustrates a typical optical zone pattern image I' produced by acousto-optic modulator 50 with a single transducer 54.

Focusing will occur at a distance $b_n \approx d_n^2/2n\lambda$, where $d_n$ is the distance from the $n^{th}$ zone to the zero order zone. Thus, a change in the magnitude of $d_n$ will change the focal distance $b_n$ from the $n^{th}$ zone.

The image I' represents a segment of a larger optical zone pattern. The acousto-optic modulator 50 is programmed to produce one such segment at a time. Scanning of the ultrasonic beam is accomplished by changing the zone pattern image to include a greater number of higher order zones or a greater number of lower order zones. The higher order zones are narrower and closer together thus causing larger phase shifts, which result in larger deflection angles. On the other hand, the lower order zones are wider and farther apart resulting in smaller phase shifts and consequently smaller deflection angles.

Thus for a given focal length, if the modulating chirp signal S is continuously modified so that the image I' has higher and higher order lines, then the ultrasonic beam E' will scan farther from the horizontal. Likewise, if chirp signal S is continuously modified so that image I' has lower and lower order lines, then the ultrasonic beam E' will scan closer to the horizontal. It should be noted that the chirp signal S can also be modified so that the image I' of FIG. 5 would appear inverted, that is with the higher order lines at the bottom. Thus it can be seen that the beam E' can be made to scan on either side of the horizontal.

The pulsed laser beam A' must be synchronized with the presence of the acoustic stress wave W in the column 52. This may be accomplished by such methods as a special synchronizing circuit 60 or by choosing a laser pulse width which is wide compared to the duration of chirp signal S.

Some of the many advantages and new features of the subject invention should now be apparent in view of the foregoing description. For example, an ultrasonic beam having a wavelength which is sufficiently small to detect small defects and abnormalities in a sample can be generated. Moreover, this ultrasonic beam may be quickly and easily focused and scanned over the sample without the need for bulky or expensive equipment.

Numerous additional modifications and variations of the subject invention are possible in light of the above teachings. For example, a high power flash lamp could be substituted for the pulsed laser. It is therefore to be understood that within the scope of the appended claims, the invention may be practiced otherwise than as specifically described herein.

What is claimed is:

1. Apparatus for generating a focusable and scannable ultrasonic beam for use in examining an object internally comprising in combination:
   a pulsed laser for generating a light beam;
   light modifying means optically connected to said light means for producing an optical zone pattern having alternating light and dark zones in said light beam, said light modifying means including, an optical mask having alternating reflecting and transmitting ring zones, said ring zones having radii determined by a preselected acoustic wavelength in a predetermined propagation medium, an optial lens slidably disposed in the path of the light beam after it emerges from said optical mask for forming an image of the optical zone pattern on a focal plane, and an oscillatable mirror disposed in the path of the light beam after the lens for scanning the light beam; and
   light absorbing means disposed in the path of light beam and in contact with a propagation medium surrounding the object to be examined for propagating an ultrasonic beam through said medium when an image of the optical zone pattern is formed on said light absorbing means.

2. Apparatus as recited in claim 1 wherein the light absorbing means further comprises a layer of thermoelastic material having a high coefficient of thermal expansion.

3. Apparatus for examining an object for internal flaws and abnormalities comprising in combination: a pulsed laser for generating a light beam;
   light modifying means optically connected to said light means for producing an optical zone pattern having alternating light and dark regions in said light beam, said light modifying means including, an optical mask having alternating reflecting and transmitting ring zones, said ring zones having radii determined by a predetermined acoustic wavelength in a preselected propagation medium, an optical lens slidably disposed in the path of the light beam after it emerges from said optical mask for forming an image of the optical zone pattern on a focal plane, and an oscillating mirror disposed in the path of the light beam after the lens for scanning the light beam;
   an acoustic propagation medium surrounding the object to be examined;
   light absorbing means disposed in the path of said light beam and in contact with said propagation medium for propagating an ultrasonic beam through said medium when an image of the optical zone pattern is formed on said light absorbing means;
   detector means for both receiving the ultrasonic beam after it has passed through the object and converting said beam to an electrical signal; and
   electronic means for analyzing the electrical signal from said detector means, whereby interior flaws and abnormalities of the object may be determined.

4. Apparatus as recited in claim 3 wherein the light absorbing means further comprises a layer of thermoelastic material having a high coefficient of thermal expansion.

5. Apparatus for generating a focusable and scannable ultrasonic beam for use in examining an object internally, comprising:
   light means for generating a light beam, said light means comprising a pulsed laser;
   light modifying means optically connected to said light means for producing an optical zone pattern having alternating light and dark zones in the light beam, said light modifying means including signal generator means for generating an acoustic chirp signal and acousto-optic means for modulating the light beam with the acoustic chirp signal; and
   light absorbing means disposed in the path of said light beam and in contact with a propagation medium surrounding the object to be examined for propagating an ultrasonic beam through said medium when an image of the optical zone pattern is formed on said light absorbing means.

6. Apparatus as recited in claim 5 wherein the acousto-optic modulating means further comprises:
   a water column disposed between the laser and the absorbing means; and
   a piezoelectric transducer disposed at one end of said water column and connected to the acoustic chirp signal generating means, whereby an acoustic wave corresponding to the chirp signal is propagated in said water column such that the index of refraction of the water is varied along the length of said water column.

7. Apparatus as recited in claim 6 wherein the acoustic chirp signal generating means comprises first electronic means for modifying the waveform of the acoustic chirp signal.

8. Apparatus as recited in claim 7 further comprising second electronic means for synchronizing the pulsed laser and the chirp signal generating means.

9. Apparatus for examining an object for internal flaws and abnormalities comprising:
- light means for generating a light beam, said light means comprising a pulsed laser;
- light modifying means optically connected to said light means for producing an optical zone pattern having alternating light and dark regions in the light beam, said light modifying means including signal generator means for generating an acoustic chirp signal, and acousto-optic means for modulating the light beam with the acoustic chirp signal;
- an acoustic propagation medium surrounding the object to be examined;
- light absorbing means disposed in the path of the light beam and in contact with said propagation medium for propagating an ultrasonic beam through said medium when an image of the optical zone pattern is formed on said light abosrbing means;
- detector means for both receiving the ultrasonic beam after it has passed through the object and converting said beam to an electrical signal; and
- electronic means for analyzing the electrical signal from said detector means, whereby interior flaws and abnormalities of the object may be determined.

10. Apparatus as recited in claim 9 wherein the acousto-optic modulating means further comprises:
- a water column disposed between the laser and the absorbing means; and
- a piezoelectric transducer disposed at one end of said water column and connected to the acoustic chirp signal generating means, whereby an acoustic wave corresponding to the chirp signal is propagated in said water column such that the index of refraction of the water is varied along the length of said water column.

11. Apparatus as recited in claim 10 wherein the acoustic chirp signal generating means comprises first electronic means for modifying the waveform of the acoustic chirp signal.

12. Apparatus as recited in claim 11 further comprising second electronic means for synchronizing the pulsed laser and the chirp signal generating means.

13. Apparatus as recited in claim 12 wherein the detector means comprises a hydrophone.

* * * * *